United States Patent [19]

Dietl

[11] Patent Number: 5,527,537
[45] Date of Patent: Jun. 18, 1996

[54] PHARMACEUTICAL PREPARATION CONTAINING CYCLOSPORINE(S) FOR INTRAVENOUS ADMINISTRATION AND A PROCESS FOR ITS PRODUCTION

[76] Inventor: Hans Dietl, Eichendorffstrasse 33, Bad Aibling, Germany, 8202

[21] Appl. No.: 60,564

[22] Filed: May 12, 1993

[30] Foreign Application Priority Data

May 18, 1992 [DE] Germany .................. 42 16 373.0

[51] Int. Cl.$^6$ ............... A61K 9/127; B01J 13/02
[52] U.S. Cl. ................ 424/450; 436/829; 264/4.1
[58] Field of Search ................ 424/450, 451, 424/455; 514/9, 11, 15; 436/829; 264/4.1

[56] References Cited

U.S. PATENT DOCUMENTS

| | | | |
|---|---|---|---|
| 4,388,307 | 6/1983 | Cavanak | 424/177 |
| 5,206,219 | 4/1993 | Desai | 424/455 |
| 5,294,604 | 3/1994 | Nussemblatt et al. | 514/11 |

FOREIGN PATENT DOCUMENTS

| | | |
|---|---|---|
| 0361928A2 | 4/1990 | European Pat. Off. |
| 0391369A2 | 4/1990 | European Pat. Off. ........ A61K 9/107 |
| 0391369 | 10/1990 | European Pat. Off. |

OTHER PUBLICATIONS

WPI/print out No. 86–335072. Mizushima. 1 page.
WPI/print out No. 92–352740. Green Cross Corp. 1 page.
A. Tibell, et al. Cyclosporine A in Fat Emulsion Carrier: Immunosuppressive Effect in Vitro. Scand. J. Immunol. 35. pp. 231–236. 1992.

A. Yanagawa, et al. Selective transfer of cyclosporin to thoracic lymphatic systems by the application of lipid microspheres. J. Microencapsulation, 1989, vol. 6, No. 2. pp. 161–164.

W. Homan, et al. Studies On The Immunosuppressive Properties of Cyclosporin A In Rats Receiving Renal Allografts. Transplantation. vol. 29, No. 5. pp. 361–366.

Y. Mizushima. Lipid Microspheres As Novel Drug Carriers. Drugs Exptl. Clin. Res XI(9). 1985. pp. 595–600.

A. Shah, et al. Effect of Co–Administration of Intralipid™ On the Pharmacokinetics of Cyclosporine In the Rabbit. Biopharmaceutics & Drug Disposition. vol. 12. 1991. pp. 457–466.

Abstract No. 86–335071/51, Teikoku Hormone Mfg. Ltd., Japan, Apr. 26, 1985.

J. Pharm Sci, Bd 79, Nr 3, 1919, S Venkataram, "Pharmacokinetics of two alternative dosage forms of cyclosporine: Liposomes and Intralipid".

*Primary Examiner*—Carlos Azpuru
*Attorney, Agent, or Firm*—Townsend and Townsend and Crew

[57] ABSTRACT

A pharmaceutical preparation is disclosed which contains one or several cyclosporine(s), one or several natural oils, 3-sn-phosphatidyl choline and/or phosphatidyl ethanol amine and water.

17 Claims, 1 Drawing Sheet

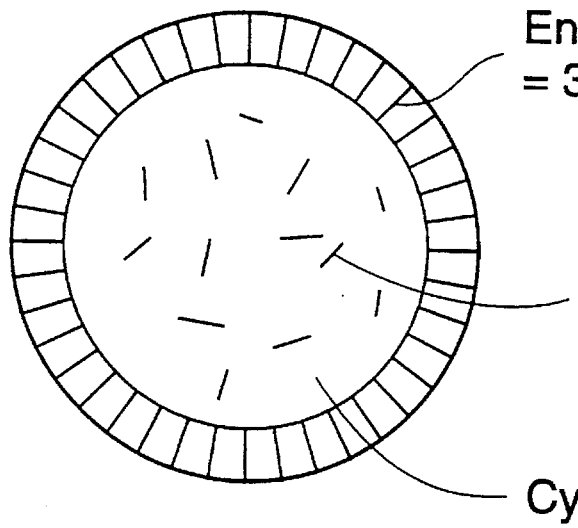

Envelope (phospholipid
= 3-sn-phosphatidyl choline)

Cyclosporine microcrystals

Cyclosporine dissolved in oil

*Fig. 1*

PHARMACEUTICAL PREPARATION CONTAINING CYCLOSPORINE(S) FOR INTRAVENOUS ADMINISTRATION AND A PROCESS FOR ITS PRODUCTION

BACKGROUND OF THE INVENTION

The invention relates to a new pharmaceutical preparation containing cyclosporine(s), a production process for this pharmaceutical preparation and its use for intravenous administration.

Cyclosporines are cyclic oligopeptides from lower fungi, which were discovered by scientists of Sandoz AG, Basel. Particularly, cyclosporine A or cyclosporine B are used as immunosuppressants, in particular in organ transplantations. Moreover, the cyclosporine derivative "SDZ IMM 125", a hydroxy ethyl derivative of D-serine-8-cyclosporine, is preferred. The application for other diseases, e.g. diabetes and psoriasis and numerous autoimmune diseases (e.g. rheumatoid arthritis, endogenous uveitis, etc.) has also been described.

The most known cyclosporine is cyclosporine A (formula: $C_{62}H_{111}N_{11}O_{12}$).

Cyclosporine A is obtained as a white amorphous powder by means of column chromatography over silica gel from fungi, it crystallizes from acetone in white needles having a melting point of 148° to 151° C. In addition to cyclosporine A, numerous other cyclosporines ranging from cyclosporine A to cyclosporine Z are known (Römpps Chemie Lexikon, 9th edition, pages 841 to 843).

Semisynthetic derivatives of cyclosporine are known and can be used according to the invention. These are substances which are very similar to each other in chemical respect, which consist of cyclic polypeptides of 11 partly methylated amino acids. Cyclosporines are soluble in alcohol, ether, acetone and chlorinated hydrocarbons and natural oils (triglycerides of fatty acids).

Cyclosporine A is described and commercially available as a solution for oral administration, which is dissolved in a mixture of alcohol with a vegetable oil (Pharmacopoeia Martindale, 29th edition, US Pharm. XXII, 619).

In addition to oral administration, the intravenous administration of cyclosporine A is in particular also of importance, since, above all, directly after organ transplantations, an oral administration is not possible. Since cyclosporines are insoluble in an aqueous medium, cyclosporine is dissolved in a mixture of alocohol and poly(oxyethylene)-40-castor oil, diluted prior to administration with saline solution or glucose solution and slowly infused for intravenous administration.

A cyclosporine concentrate for injection is described in the United States Pharmacopoeia XXII, 619), which is to be a sterile solution of cyclosporine in a mixture of alcohol with a suited vegetable oil. This form of presentation is not only unsuited for injections, but even lethal, since a critical embolism may immediately occur, if an oil is injected in this form.

Consequently, the intravenously applicable form of cyclosporine A is only commercially available in the form of the aforementioned concentrate with alcohol and poly(oxyethylene)-40-castor oil as Sandimmun® infusion concentrate. The adjuvants alcohol and poly(oxyethylene)- 40-castor oil used for dissolving cyclosporine A are not only no ideal, but even dangerous adjuvants. Due to the content of alcohol, there is a health risk above all for persons suffering from a liver disease, alcoholics, epileptics, brain-injured persons, pregnant women and children. Poly(oxyethylene)-40-castor oil in injection and infusion solutions can lead to hypersensitivity reactions particularly in persons with susceptibility to allergic diseases or in persons to whom a preparation containing poly(oxyethylene)-40-castor oil has already been administered as an injection or infusion a short time ago, which can manifest themselves as a decrease in blood pressure, defective circulation with blueness of the lips and finger nails, dyspnoea and hot flushes with temporary blushing of the skin. These reactions can differ in terms of time and extent and also lead to life-threatening conditions. Moreover, an increase in the lipids in the blood with pathological shifting of the lipoprotein pattern, an impairment of the flow properties of the blood and of the aggregation ability of the erythrocytes may occur in the case of a long-term administration. (Technical Information of Sandimmun®; attention in the case of poly(oxyethylene)-40-castor oil in injection and infusion solutions, Deutsche Apothekerzeitung 125, 769 (1985), Pharmakopoeia Martindale, 29th edition (1989), 614 to 619). Poly(oxyethylene)-40-castor oil (e.g. Cremophor® EL) is a non-ionic emulsifier produced by reacting 35 moles of ethylene oxide with 1 mole of castor oil. Cremophor EL is not covered by the natural oils and, as opposed to them, is soluble in water.

Consequently, it is of great importance to have cyclosporine-containing injection solutions or infusion solutions available, which neither contain alcohol nor poly(oxyethylene)-40-castor oil and which, nevertheless, contain cyclosporine in a therapeutically sufficient amount and are also well tolerable and can be administered without the side effects described above.

Although these problems have been known for more than ten years, so far nobody has succeeded in making available a suited injection solution or infusion solution with cyclosporines for intravenous administration despite all efforts.

SUMMARY OF THE INVENTION

Consequently, an object of the present invention is to provide a pharmaceutical preparation containing cyclosporine(s), which contains neither alcohol nor poly(oxyethelene)- 40-castor oil and which is suited for intravenous administration.

According to the invention this object is attained by providing a pharmaceutical preparation containing cyclosporine(s) which contains one or several cyclosporine(s), one or more natural oils, 3-sn-phosphatidyl choline and/or phosphatidyl ethanol amine and water.

Thus, the present invention solves surprisingly the problem of the side effects described above by producing a cyclosporine-containing injection solution or infusion solution, in which the cyclosporine is contained in a therapeutically sufficient concentration in an intravenously applicable mixture of natural triglycerides and water and 3-sn-phosphatidyl cholines. A further completely surprising advantage—in addition to the absence of the untolerable adjuvants alcohol and poly(oxyethylene)-40-castor oil—consists in its increased therapeutic effectiveness with the pharmaceutical preparation according to the invention. Thus, the dose of cyclosporine(s) can be reduced and, accordingly, the frequency and seriousness of the side effects. A possible explanation of this could be that the cyclosporine is dissolved in a microsphere of a fatty particle in the presentation form according to the invention, and this fatty particle with the cyclosporine incorporated therein gets to an essential degree directly to the area where the cyclosporine takes effect, the lymphocytes. Only there the microsphere of the fatty particle, which has been intact up to that moment, is probably decomposed, and the cyclosporine is released directly and completely at the area where it takes effect, whereas, as opposed to this, cyclosporine is distributed in the entire organism unspecifically in the former customary presentation form. Cyclosporine is certainly effective in numerous possible application possibilities, e.g. in diabetes, rheumatoid arthritis, psoriasis, other autoimmune diseases, but limited in the application due to the dose-dependent side effects. The pharmaceutical preparation containing the cyclosporine(s) according to the invention provides the possibility of bringing the cyclosporine directly and in targeted fashion to the actual "area where it takes effect", the immune system, whereby the application possibilities can be considerably increased.

BRIEF DESCRIPTION OF THE DRAWING

The enclosed FIG. 1 shows in schematic form the structure of the fatty particle according to the invention, which contains cyclosporine.

DETAILED DESCRIPTION OF THE INVENTION AND PREFERRED EMBODIMENTS

The pharmaceutical preparation for intravenous administration according to the invention contains a therapeutic amount of a cyclosporine or several cyclosporines, a pharmaceutically tolerable oil, 3-sn-phosphatidyl choline and, possibly, an alkali salt of a free fatty acid and a substance for making the mixture isotonic, e.g. glycerin and/or sorbitol and/or xylitol.

Fatty emulsions which can be intravenously administered for parental nutrition and processes for the production are known from the prior art (e.g. DE-PS 1 249 454, GB-PS 2 406 621, DE-OS 3 721 137, EP 071 995, DE-OS 3 032 300). The production of fatty emulsions using natural oils and phosphatidyl cholines as emulsifiers is described in these publications.

These fatty emulsions are oil-in-water emulsions, in which the droplet size of the individual fat droplets is less than 4 microns so that these emulsions can be infused without the risk of an embolism.

Soy bean oil and/or safflower oil and/or MCT oils (medium-chain triglycerides=coconut oil) are used as oils, the phosphatidyl cholines are used in the form of soy lecithin and preferably egg lecithin. The oils are emulsified in an aqueous solution, whereafter the mixture is homogenized to an emulsion with a particle size of less than 4 microns (DE-PS 1 249 454).

Since cyclosporines are soluble in natural oils, it could be considered obvious to simply dissolve cyclosporines in such commercial fatty emulsions (trade names: Intralipid®, Lipovenös®, Liposyn® by the addition of crystallized cyclosporine. However, this does not succeed, since even after thorough stirring the by far predominant part of the cyclosporine is still present in the form of undissolved crystals. This is undoubtedly attributable to the fact that the cyclosporine cannot penetrate the lipid membrane, i.e. a "loading" of the fatty droplets of the fatty emulsions is not possible. Consequently, both a completely inadequate, therapeutically not sufficient concentration of cyclosporine in the solution and solid particles in the solution are obtained, which may possibly have a life-threatening effect on the patient if administered intravenously. Although the harmfulness of the adjuvants alcohol and poly(oxyethylene)-40-castor oil contained in the concentrate containing cyclosporine has been known for a long time, so far one did not succeed in solving the problem.

Now it has been surprisingly found according to the invention that it is very well possible to produce an intravenously applicable administration form of cyclosporine(s) without alcohol and without poly(oxyethylene)- 40-castor oil in the form of an emulsion of cyclosporines in natural, pharmaceutically tolerable oils, 3-sn-phosphatidyl choline and water. It is decisive that the cyclosporine is first of all completely dissolved in the used oil, subsequently emulsified using 3-sn-phosphatidyl choline, preferably in the form of egg lecithin, and that the mixture is homogenized to an emulsion having a particle size of less than 4 microns, preferably between 0.2 to 0.7 µm, as an average.

After the subsequent sterilization, a stable injection solution or infusion solution with a therapeutically applicable concentration of cyclosporine(s) is obtained.

Natural and synthetic cyclosporines, e.g. the known cyclosporines A to Z can be used as cyclosporines; cyclosporine A and cyclosporine G and the cyclosporine derivative SDZ IMM 125 are preferred.

The following can be used as natural oils: soy bean oil, safflower oil (safflower seed oil), coconut oil (MCT oils), fish oils, corn oil, olive oil, etc. Soy bean oil is preferred. The used oil must be as free as possible from peroxides. The poly(oxyethylene)-40-castor oil known from the prior art is a synthetic derivative and cannot be used according to the invention.

The used cyclosporine, e.g. cyclosporine A, is first of all dissolved in the oil, e.g. soy bean oil, the concentration of the cyclosporine in the oil being in general between 0.2 to 7.0% by weight, preferably between 1 to 5% by weight. The dissolution is carried out in known fashion by mixing and stirring the cyclosporine in the oil. Care should be taken that the presence of oxygen is excluded in order to avoid an oxidation.

Oxygen-free water is now added to the cyclosporine-containing, oily solution and 3-sn-phosphatidyl choline, preferably in the form of egg lecithin and/or soy lecithin, is added as an emulsifier. 4 to 20 parts of the 3-sn-phosphatidyl choline are in general added to 100 parts of oil.

Egg lecithin with a content of 3-sn-phosphatidyl choline of 60 to 85% is especially preferred. The 3-sn-phosphatidyl choline may also be partly hydrogenated.

Egg lecithin and/or soy lecithin, particularly egg lecithin, are preferred as suppliers of 3-sn-phosphatidyl choline of the partially hydrogenated 3-sn-phosphatidyl choline or hydrogenated 3-sn-phosphatidyl choline. Lecithins with a content of more than 60% of 3-sn-phosphatidyl choline and/or partially hydrogenated 3-sn-phosphatidyl choline and/or hydrogenated 3-sn-phosphatidyl choline are above all suited.

If required, an alkali salt of a free fatty acid with 6 to 26 carbon atoms may also be added in order to adjust the pH value to 5 to 9 and to facilitate the emulsification and later homogenization. The sodium or potassium salts of palmitic acid, palmitoleic acid, stearic acid, oleic acid, linoleic acid and linolenic acid are especially preferred.

The mixture which now contains cyclosporine, natural oil, 3-sn-phosphatidyl choline, water and, possibly, an alkali salt of a free fatty acid is now diluted with water until the oil accounts for 5 to 40% of the total weight.

Now a crude emulsion is produced by means of vigorous stirring, preferably with an Ultra-Turrax.

In order to ensure that the solution is hemisotonic, a corresponding amount of glycerin and/or sorbitol and/or xylitol may be possibly be added.

This crude emulsion is now homogenized in a high-pressure homogenizer at pressures between 100 to 500 bar, possibly several times, until an emulsion is obtained, in which the particle size of all particles is less than 4 microns, preferably less than 1.5 microns (98% of all particles).

Thereafter, the emulsion is diluted to the desired concentration by adding water. Subsequently, the emulsion is filled into suited receptacles, e.g. bottles or ampoules, and heat-sterilized.

The cyclosporine contained in the intravenously applicable drug form is customarily and preferably present in completely dissolved form. The cyclosporine, dissolved in oil, is contained in the interior of a fatty particle, the oil being enclosed by an envelope consisting substantially of phospholipid (3-sn-phosphatidyl choline). However, it is also possible to use the cyclosporine in such a high concentration during production that only part of the cyclosporine is present in dissolved form, but another part is in the interior of the fatty particle in solid form. Due to the envelope surrounding the fatty particle, which cannot be penetrated by the solid cyclosprine, even solid cyclosporine can thus be infused.

The production of such drug forms is carried out according to the process of the invention in such fashion that the oil used according to the invention is heated to e.g. approx. 50° to 70° C. and then cyclosporine is added in such an amount that a solution which is almost saturated at this higher temperature is formed; then the intravenous drug form is produced in accordance with the process of the invention.

Part of the originally used cyclosporine can precipitate in the case of longer storage at room temperature or lower temperatures. However, this precipitated, microcrystalline cyclosporine remains in the fatty particle and does not penetrate into the aqueous phase as a solid crystal. Thus, highly concentration drug forms according to the invention can be produced, which are particularly suited as concentrates to be diluted prior to use.

The following examples of embodiment describe the mixture according to the invention and the process for its production in detail. However, the invention is not restricted to this.

EXAMPLE 1

10.0 kg of winterized soy bean oil (neutral pH value, free from peroxide) is gassed with nitrogen, and heated to about 50° C. with stirring and further gassing with nitrogen. A winterized soy bean oil is a soy bean oil, which has been cooled to less than −10° C. prior to the use so that insoluble shares are precipitated in the cold, which are filtered off.

Now, 400 g of cyclosporine A is added to this soy bean oil and dissolved with stirring.

2.5 kg of glycerin and 10 l of water are introduced into a second receptacle. Gassing with nitrogen is carried out until the oxygen content of the mixture is less than 0.5 mg/l.

1.2 kg egg lecithin (iodine number 60 to 70) with a content of about 80% of 3-sn-phosphatidyl choline and about 12% phosphatidyl ethanol amine (cephalin) and 40 g of sodium oleate are added.

A crude emulsion is produced at a temperature of about 50° C. by vigourous stirring with an Ultra-Turrax.

Now, the soy bean oil with the cyclosporine A dissolved therein is transferred into this second receptacle through a fat-resistant, germ-proof filter with a pore size of about 50 microns, and vigourously stirred with an Ultra-Turrax for further 10 minutes at about 50° C. The pH value is checked and should be between 5 and 9, preferably between 7.0 and 8.5. If this is not the case, a small amount of sodium oleate is possibly still added.

The obtained crude emsulsion is filtered through a special-steel filter (pore size between 5 and 50 microns) and subsequently homogenized with a 2-stage high-pressure homogenizer with 3 pistons (1st stage 100 bar, 2nd stage 400 bar). The required homogenization pressure is built up with water for injection purposes, not with the crude emulsion in order to avoid a soiling and deposition of oil droplets.

The process of homogenization is repeated that many times until the desired particle size is achieved. No particle must be greater than 4 microns. The diameter of the particles is 0.2 to 0.6 microns on average.

In order to achieve a particle size which can be well used, it is in general necessary to repeat the process of homogenization four times. The emulsion should be cooled to 30° to 50° C. after each homogenization process.

The emulsion is added to 57 l of oxygen-free water ad injectabilia. Gassing with nitrogen is again carried out until the oxygen content is less than 0.5 mg/l.

18.5 l of water ad injectabilia are passed through the homogenizer at 400 bar as additional water, and then added to the aforementioned total amount. Gassing with nitrogen of the entire batch is continued until the oxygen content is less than 0.5 mg/l. Prior to the filling into glass bottles, filtration through a special-steel filter with a mean pore size of 5 microns is carried out. The filtration pressure should not exceed 0.2 bar so that a breaking of the emulsion is prevented.

The particle size and the particle distribution are determined under a microscope or a Coulter counter. The particle size distribution is:

| Particle size | Number of particles |
|---|---|
| <0.2 microns | 34% |
| 0.2–0.5 microns | 43% |
| 0.5–0.9 microns | 14% |
| 0.9–1.2 microns | 6% |
| 1.2–1.9 microns | 2% |
| 1.9–2.2 microns | less than 1% |
| 2.2–2.5 microns | less than 1% |
| 2.5–3.2 microns | less than 1% |
| >3.2 microns | less than 1% |

The emulsion is filled into 100 ml glass bottles. Prior to the filling, the bottles are gassed with nitrogen. It is advantageous to cool the used nitrogen to minus 20° to 30° C. so that the nitrogen sinks more easily to the bottom of the bottle. Gassing of the bottles should be continued during the filling of the bottles, as well.

The obtained emulsion is heat-sterilized at 121° C. for 20 minutes. A so-called rotation autoclave is advantageously used, in which the bottles rotate slowly overhead during the sterilization. Due to this, the time necessary for filling and cooling is reduced, and it is avoided that the particle size is changed. A sterile, intravenously applicable emulsion with a content of 400 mg of cyclosporine A/100 ml is obtained. The particle distribution after sterilization is indicated as follows:

| Particle size | Number of particles | |
|---|---|---|
| <0.2 microns | | 25% |
| 0.2–0.5 microns | | 46% |
| 0.5–0.9 microns | | 19% |
| 0.9–1.2 microns | | 6% |
| 1.2–1.5 microns | | 2% |
| 1.5–1.9 microns | less than | 1% |
| 1.9–2.2 microns | less than | 1% |
| 2.2–3.2 microns | less than | 1% |
| >3.2 microns | | 0% |

The sterile emulsion obtained in this fashion can be slowly infused in patients for 2 to 6 hours, a total of 400 mg of cyclosporine A being infused as therapeutically optimum maximum dose.

The infusion solution contains per 100 ml:

| | |
|---|---|
| Cyclosporine A: | 400 mg |
| Soy bean oil: | 10 mg |
| Egg lecithin: | 1.2 g |
| Glycerin: | 2.5 g |
| Sodium oleate: | 40 mg |
| and water ad | 100 ml |

EXAMPLE 2

The process of example 1 is repeated, using a fish oil concentrate instead of the soy bean oil which contains 18% eicosapentaenoic acid and 12% docosahexaenoic acid. A pharmaceutical preparation for intravenous application with the following composition per 100 ml is obtained:

| | |
|---|---|
| Cyclosporine A: | 400 mg |
| Fish oil concentrate: | 10 g |
| Egg lecithin: | 1.2 g |
| Glycerin: | 2.5 g |
| Sodium oleate: | 40 mg |
| Water ad injectabilia ad | 100 ml |

| Particle size | Number of particles |
|---|---|
| 0.2 microns | approx. 25% |
| 0.2–0.5 microns | approx. 46% |
| 0.5–0.9 microns | approx. 19% |
| 0.9–1.2 microns | approx. 6% |
| 1.2–1.5 microns | approx. 2% |
| 1.5–1.9 microns | less than 1% |
| 1.9–2.2 microns | less than 1% |

EXAMPLE 3

The process according to example 1 is repeated, 250 g of cyclosporine A being, however, weighed in per 10 kg of soy bean oil.

A pharmaceutical preparation for the intravenous administration with the following composition per 100 ml:

| | |
|---|---|
| Cyclosporine A: | 250 mg |
| Soy bean oil: | 10 g |
| Egg lecithin: | 1.2 g |
| Glycerin: | 2.5 g |
| Sodium oleate: | 40 mg |
| Water ad injectabilia ad | 100 ml |

| Particle size | Number of particles |
|---|---|
| 0.2 microns | approx. 24% |
| 0.2–0.5 microns | approx. 58% |
| 0.5–0.9 microns | approx. 16% |
| 0.9–1.2 microns | approx. 2% |
| 1.2–1.5 microns | less than 1% |
| 1.5–1.9 microns | less than 1% |

EXAMPLE 4

Example 1 is repeated using an egg lecithin with a content of 3-sn-phosphatidyl choline of about 70% and a content of cephalin of about 20% instead of the egg lecithin used in example 1. 50 mg of sodium oleate are used instead of 40 mg of sodium oleate. A pharmaceutical preparation for intravenous administration with the following composition per 100 ml is obtained.

| | |
|---|---|
| Cyclosporine A: | 400 mg |
| Soy bean oil concentrate | 10 g |
| Egg lecithin: | 1.2 g |
| Glycerin: | 2.5 g |
| Sodium oleate: | 50 mg |
| Water ad injectabilia ad | 100 ml |

| Particle size | Number of particles |
|---|---|
| 0.2 microns | approx. 30% |
| 0.2–0.5 microns | approx. 49% |
| 0.5–0.9 microns | 17% |
| 0.9–1.2 microns | 3% |
| 1.2–1.5 microns | less than 1% |
| 1.5–1.9 microns | less than 1% |

EXAMPLE 5

Example 1 is repeated using a partially hydrogenated egg lecithin with about 80% of partially hydrogenated 3-sn-phosphatidyl choline with a iodine number of 35 (example 1: iodine number 60 to 70) instead of the egg lecithin and 50 g of sodium oleate. A pharmaceutical preparation for intravenous administration with the following composition per 100 ml is obtained.

| | |
|---|---|
| Cyclosporine A: | 400 mg |
| Soy bean oil: | 10 g |
| Egg lecithin (partially hydrogenated): | 1.2 g |
| Glycerin: | 2.5 g |
| Sodium oleate: | 50 mg |
| Water ad injectabilia ad | 100 ml |

| Particle size | Number of particles |
|---|---|
| 0.2 microns | approx. 10% |
| 0.2–0.5 microns | approx. 63% |
| 0.5–0.8 microns | approx. 23% |
| 0.8–1.2 microns | approx. 4% |
| 1.2–1.5 microns | less than 1% |
| 1.5–1.9 microns | less than 1% |
| 1.9–2.2 microns | less than 1% |
| 2.2–3.2 microns | less than 1% |
| >3.2 microns | 0% |

EXAMPLE 6

Example 1 is repeated using soy bean lecitin with a content of about 75% of 3-sn-phosphatidyl choline instead of the egg lecithin.

EXAMPLE 7

10.0 kg of winterized soybean oil is gassed with nitrogen and heated to about 50° to 60° C. with stirring. A determination of the free fatty acids in the soy bean oil showed a content of free fatty acids of 2.5 meq/l. The pH value is about 3.5 to 4.5.

500 g of cyclosporine A are added and dissolved with stirring. 10 l of water ad injectabilia, 2.5 kg of glycerin and 1.0 kg of egg lecithin with a content of about 75% of 3-sn-phosphatidyl choline at a temperature of about 50° C. are added. A crude emulsion is produced by vigourous stirring, preferably with an Ultra-Turrax. A pH value of 7.5 to 8.5 is adjusted by adding a 10% sodium hydroxide solution.

The crude emulsion is filtered through a special-steel filter with a pore size of about 30 microns.

Subsequently, homogenization is carried out with a 2-stage high-pressure homogenizer with three pistons (1st stage 100 bar; 2nd stage 450 bar). The required homogenization pressure is built up with water ad injectabilia.

The homogenization procedure is carried out for a total of four times at a temperature of 30° to 60° C.

10 l of water ad injectabilia are added to the emulsion, and gassing with nitrogen is carried out with stirring until the oxygen content is less than 0.5 ml/l. 6.5 l of water ad injectabilia are now passed through the homogenizer as additional water at 450 bar and added to the total amount. Gassing with nitrogen is continued until the oxygen content is less than 0.5 mg/l.

Filtration is carried out through a special-steel filter with a mean pore width of 5 microns, care being taken that the filtration pressure is not more than 0.2 bar.

The emulsion is filled into ampoules of 20 ml and sterilized at 120° C. for 20 minutes.

An examination of the particle size showed the following distribution:

| Particle size | Number of particles |
| --- | --- |
| <0.2 microns | 24% |
| 0.2–0.5 microns | 58% |
| 0.5–0.9 microns | 16% |
| 1.2–1.5 microns | less than 1% |
| 1.5–1.9 microns | less than 1% |
| >2.0 microns | 0% |

The obtained pharmaceutical preparation for intravenous administration contains 250 mg of cyclosporine A per ampoule (20 ml). Prior to administration, the content of the ampoule is diluted by adding it to a commercially available 10% fatty emulsion in the ratio of 1:5 to 1:10, and then it is slowly infused.

EXAMPLE 8

Example 7 is repeated using, however, 250 g of cyclosporine A plus 250 g of cyclosporine G instead of 500 g of cyclosporine A.

Then, an ampoule with 20 ml contains 125 mg of cyclosporine A and 125 g of cyclosporine G.

EXAMPLE 9

A pharmaceutical preparation containing cyclosporine is produced as described in example 1, using, however, 150 g of SDZ IMM 125, a hydroxy ethyl derivative of D-serine-8-cyclosporine instead of cyclosporine A. The production and the structure of SDZ IMM 125 are described in G. Baumann et al., Transplantation Proceedings, vol. 24, No. 4, Suppl. 2 (1992), pages 43 to 48 and P. C. Hiestand et al., Transplantation Proceedings, vol. 24, No. 4, Suppl. 2, pages 31 to 38 (1992). A sterile emulsion with a content of 150 mg of the described cyclosporine derivative per 100 ml of the emulsion, which can be administered intravenously, is obtained.

I claim:

1. A pharmaceutical preparation for intravenous administration consisting essentially of the following components:
   (a) at least one cyclosporine selected from the group consisting of natural cyclosporines, synthetic cyclosporines, and semi-synthetic cyclosporines,
   (b) at least one natural oil, essentially free of peroxides,
   (c) at least one member selected from the group consisting of 3-sn-phosphatidyl choline, phosphatidyl ethanol amine, egg lecithin containing 3-sn-phosphatidyl choline, soy lecithin containing 3-sn-phosphatidyl choline, hydrogenated forms, and partially hydrogenated forms thereof,
   (d) pharmaceutically tolerable alkali salts of free fatty acids, and
   (e) water,
wherein component (a) is dissolved in component (b) and component (b) is enclosed in the interior of fatty particles in which component (b) is surrounded by an envelope of component (c), said fatty particles being emulsified in water, the pharmaceutical preparation being essentially free of poly(oxyethylene)-40-castor oil and alcohol.

2. A pharmaceutical preparation according to claim 1, wherein component (c) is at least one member selected from the group consisting of egg lecithin containing 3-sn-phosphatidyl choline, and soy lecithin containing 3-sn-phosphatidyl choline.

3. A pharmaceutical preparation according to claim 1, wherein component (c) is a member selected from the group consisting of 3-sn-phosphatidyl choline, phosphatidyl ethanol amine, egg lecithin containing 3-sn-phosphatidyl choline, and soybean lecithin containing 3-sn-phosphatidyl choline, hydrogenated forms, and partially hydrogenated forms thereof.

4. A pharmaceutical preparation according to claim 1, wherein component (c) is a member selected from the group consisting of partially hydrogenated soy lecithin containing 3-sn-phosphatidyl choline and partially hydrogenated egg lecithin containing 3-sn-phosphatidyl choline.

5. A pharmaceutical preparation according to claim 1, wherein component (c) is egg lecithin containing at least 60% by weight of 3-sn-phosphatidyl choline.

6. A pharmaceutical preparation according to claim 1, wherein component (c) is 3-sn-phosphatidyl choline at a concentration of 0.3 to 4% by weight relative to said pharmaceutical preparation.

7. A pharmaceutical preparation according to claim 2, wherein component (c) is a member selected from the group consisting of egg lecithin containing 3-sn-phosphatidyl choline, and soy lecithin containing 3-sn-phosphatidyl choline, and amounts to 0.5 to 6.5% by weight relative to said pharmaceutical preparation.

8. A pharmaceutical preparation according to claim 1, wherein component (b) is at least one member selected from the group consisting of soy oil, safflower oil, medium-chain triglycerides, corn oil, wheat germ oil, sunflower oil, olive oil and fish oil.

9. A pharmaceutical preparation according to claim 1, wherein the concentration of component (a) relative to components (a) and (b) is between 0.2 and 7.0% by weight.

10. A pharmaceutical preparation according to claim 1, wherein component (b) amounts to 5 to 40% of the total weight of the pharmaceutical preparation.

11. A pharmaceutical preparation according to claim 1, in which said free fatty acids are at least one member selected from the group consisting of palmitic acid, palmitoleic acid, linoleic acid, linolenic acid, and alkali salts thereof.

12. A pharmaceutical preparation according to claim 1, wherein component (a) amounts to 0.01 to 0.15% by weight relative to said pharmaceutical preparation.

13. A pharmaceutical preparation according to claim 1, wherein component (d) amounts to 60 to 95% by weight relative to said pharmaceutical preparation.

14. A pharmaceutical preparation according to claim 1, consisting essentially of the following components:

(a) at least one cyclosporine, (b) at least one natural oil, (c) at least one member selected from the group consisting of 3-sn-phosphatidyl choline, phosphatidyl ethanol amine, egg lecithin containing 3-sn-phosphatidyl choline, soy lecithin containing 3-sn-phosphatidyl choline, hydrogenated forms and partially hydrogenated forms thereof, (d) pharmaceutically tolerable alkali salts of free fatty acids, (e) water, and (f) glycerin in an amount which renders said pharmaceutical preparation isotonic, wherein component (a) is dissolved in component (b) and component (b) is enclosed in the interior of fatty particles in which component (b) is surrounded by an envelope of component (c), said fatty particles being emulsified in water, the pharmaceutical preparation being essentially free of poly(oxyethylene)-40-castor oil and alcohol.

15. A pharmaceutical preparation according to claim 1, wherein said at least one cyclosporine is a member selected from the group consisting of cyclosporine A, cyclosporine G, SDZ IMM 125, and combinations thereof.

16. A pharmaceutical preparation according to claim 1, wherein component (c) is egg lecithin containing 3-sn-phosphatidyl choline.

17. A pharmaceutical preparation according to claim 1, wherein component (c) is soy lecithin containing 3-sn-phosphatidyl choline.

* * * * *